(12) United States Patent
Lynn et al.

(10) Patent No.: US 9,968,738 B2
(45) Date of Patent: May 15, 2018

(54) BIOLOGICAL FLUID FILTERS WITH MOLDED FRAME AND METHODS FOR MAKING SUCH FILTERS

(71) Applicant: Fenwal, Inc., Lake Zurich, IL (US)

(72) Inventors: Daniel Lynn, Spring Grove, IL (US); Patrick Flanagan, Algonquin, IL (US); James Chrzan, Richmond, IL (US)

(73) Assignee: FENWAL, INC., Lake Zurich, IL (US)

( * ) Notice: Subject to any disclaimer, the term of this patent is extended or adjusted under 35 U.S.C. 154(b) by 385 days.

(21) Appl. No.: 14/223,831

(22) Filed: Mar. 24, 2014

(65) Prior Publication Data
US 2015/0265755 A1 Sep. 24, 2015

(51) Int. Cl.
*A61M 5/165* (2006.01)
*A61M 1/02* (2006.01)
*A61M 1/36* (2006.01)

(52) U.S. Cl.
CPC .......... *A61M 5/165* (2013.01); *A61M 1/0281* (2013.01); *A61M 1/3636* (2014.02); *A61M 2005/1655* (2013.01); *A61M 2202/0439* (2013.01); *A61M 2207/00* (2013.01)

(58) Field of Classification Search
CPC .. A61M 5/165; A61M 1/0281; A61M 1/3636; A61M 2202/0439; A61M 2207/00; A61M 2005/1655; B01D 39/083
USPC ........ 210/435, 445, 782, 645, 488; 156/242; 604/406
See application file for complete search history.

(56) References Cited

U.S. PATENT DOCUMENTS

| | | | |
|---|---|---|---|
| 2,702,034 A | 2/1955 | Walter | |
| 2,781,064 A | 2/1957 | Dawkins | |
| 3,523,408 A | 8/1970 | Rosenberg | |
| 3,631,654 A | 1/1972 | Riely | |
| 3,650,093 A | 3/1972 | Rosenberg | |
| 3,705,100 A | 12/1972 | Blatt et al. | |
| 3,752,385 A | 8/1973 | Woodgate | |
| 3,765,536 A | 10/1973 | Rosenberg | |
| 3,765,537 A | 10/1973 | Rosenberg | |
| 3,803,810 A | 4/1974 | Rosenberg | |
| 3,892,236 A | 7/1975 | Djerassi | |
| 3,905,905 A | 9/1975 | O'Leary et al. | |
| 3,935,110 A | 1/1976 | Schmid et al. | |
| 4,009,714 A | 3/1977 | Hammer | |
| 4,009,715 A | 3/1977 | Forberg et al. | |
| 4,035,304 A | 7/1977 | Watanabe | |
| 4,066,556 A | 1/1978 | Vaillancourt | |
| 4,092,246 A | 5/1978 | Kummer | |

(Continued)

FOREIGN PATENT DOCUMENTS

BE 1005193 A3 5/1993
DE 82 20 399 U1 10/1982
(Continued)

OTHER PUBLICATIONS

Partial International Search Report for International Application No. PCT/US2014/041217 dated Dec. 1, 2014.

(Continued)

*Primary Examiner* — Madeline Gonzalez
(74) *Attorney, Agent, or Firm* — Cook Alex Ltd.

(57) ABSTRACT

Flexible housing filters for filtration of fluids and methods of making such filters are disclosed. The filters include a molded frame with no peripheral seal that houses a filter medium.

21 Claims, 8 Drawing Sheets

(56) References Cited

U.S. PATENT DOCUMENTS

| | | |
|---|---|---|
| 4,136,796 A | 1/1979 | Dubois et al. |
| 4,190,426 A | 2/1980 | Ruschke |
| 4,223,695 A | 9/1980 | Muetterties |
| 4,246,107 A | 1/1981 | Takenaka et al. |
| 4,276,170 A | 6/1981 | Vaillancourt |
| 4,283,289 A | 8/1981 | Meyst et al. |
| 4,284,209 A | 8/1981 | Barbour, Jr. |
| 4,294,594 A | 10/1981 | Sloane, Jr. et al. |
| 4,330,410 A | 5/1982 | Takenaka et al. |
| 4,340,049 A | 6/1982 | Munsch |
| 4,360,435 A | 11/1982 | Bellamy et al. |
| 4,374,731 A | 2/1983 | Brown et al. |
| 4,401,567 A | 8/1983 | Shindo et al. |
| 4,416,777 A | 11/1983 | Kuroda et al. |
| 4,460,366 A | 7/1984 | Shinno |
| 4,479,762 A | 10/1984 | Bilstad et al. |
| 4,525,182 A | 6/1985 | Rising et al. |
| 4,596,657 A | 6/1986 | Wisdom |
| 4,635,467 A | 1/1987 | Hoffa et al. |
| 4,679,693 A | 7/1987 | Forman |
| 4,701,267 A * | 10/1987 | Watanabe ............... B01D 39/14 210/335 |
| 4,753,739 A | 6/1988 | Noble |
| 4,767,541 A | 8/1988 | Wisdom |
| 4,810,378 A | 3/1989 | Carmen et al. |
| 4,838,872 A | 6/1989 | Sherlock |
| 4,855,063 A | 8/1989 | Carmen et al. |
| 4,880,548 A | 11/1989 | Pall et al. |
| 4,892,668 A | 1/1990 | Harmony et al. |
| 4,896,772 A | 1/1990 | Walter et al. |
| 4,898,573 A | 2/1990 | Takenaka et al. |
| 4,906,260 A | 3/1990 | Emheiser et al. |
| 4,915,848 A | 4/1990 | Carmen et al. |
| 4,919,823 A | 4/1990 | Wisdom |
| 4,923,620 A | 5/1990 | Pall |
| 4,925,572 A | 5/1990 | Pall |
| 4,936,993 A | 6/1990 | Nomura |
| 4,936,998 A | 6/1990 | Nishimura et al. |
| 4,963,260 A * | 10/1990 | Naoi ............... A61M 1/3633 210/435 |
| 4,976,861 A | 12/1990 | Pall |
| 4,985,153 A | 1/1991 | Kuroda et al. |
| 4,997,577 A | 3/1991 | Stewart |
| 5,015,369 A | 3/1991 | Romine et al. |
| 5,071,553 A | 12/1991 | Newlin |
| 5,071,570 A | 12/1991 | Shiraki et al. |
| 5,092,996 A | 3/1992 | Spielberg |
| 5,100,564 A | 3/1992 | Pall et al. |
| 5,104,788 A | 4/1992 | Carmen et al. |
| 5,128,048 A | 7/1992 | Stewart et al. |
| 5,141,645 A | 8/1992 | Shiraki et al. |
| 5,152,905 A | 10/1992 | Pall et al. |
| 5,154,716 A | 10/1992 | Bauman et al. |
| 5,164,087 A | 11/1992 | Naoi et al. |
| 5,180,504 A | 1/1993 | Johnson et al. |
| 5,182,017 A | 1/1993 | Ippendorf |
| 5,234,593 A | 8/1993 | Kuroki et al. |
| 5,236,716 A | 8/1993 | Carmen et al. |
| 5,252,222 A | 10/1993 | Matkovich et al. |
| 5,254,248 A | 10/1993 | Nakamura |
| 5,258,127 A | 11/1993 | Gsell et al. |
| 5,269,946 A | 12/1993 | Goldhaber et al. |
| 5,286,449 A | 2/1994 | Kuroda et al. |
| 5,298,165 A | 3/1994 | Oka et al. |
| 5,302,299 A | 4/1994 | Pascale et al. |
| 5,316,674 A | 5/1994 | Pall et al. |
| 5,316,681 A | 5/1994 | Serres |
| 5,330,462 A | 7/1994 | Nakamura |
| 5,348,646 A | 9/1994 | Costello, Jr. et al. |
| 5,350,513 A | 9/1994 | Markowitz |
| 5,360,545 A | 11/1994 | Pall et al. |
| 5,362,406 A | 11/1994 | Gsell et al. |
| 5,364,526 A | 11/1994 | Matkovich et al. |
| 5,368,725 A | 11/1994 | Bredeweg et al. |
| 5,386,734 A | 2/1995 | Pusinelli |
| 5,387,187 A | 2/1995 | Fell et al. |
| 5,393,422 A | 2/1995 | Pummell |
| 5,399,268 A | 3/1995 | Pall et al. |
| 5,403,272 A | 4/1995 | Deniega et al. |
| 5,403,304 A | 4/1995 | Ishida |
| 5,405,343 A | 4/1995 | Mohr |
| 5,407,581 A | 4/1995 | Onodera et al. |
| 5,445,629 A | 8/1995 | Debrauwere et al. |
| 5,445,736 A | 8/1995 | Pall et al. |
| 5,454,946 A | 10/1995 | Heagle et al. |
| 5,456,835 A | 10/1995 | Castino et al. |
| 5,456,845 A | 10/1995 | Nishimura et al. |
| 5,472,605 A | 12/1995 | Zuk, Jr. |
| 5,476,587 A | 12/1995 | Kuroki et al. |
| 5,476,797 A | 12/1995 | Matsunaga |
| 5,478,470 A | 12/1995 | Fukuda et al. |
| 5,498,336 A | 3/1996 | Katsurada et al. |
| 5,501,795 A | 3/1996 | Pall et al. |
| 5,507,904 A | 4/1996 | Fisher et al. |
| 5,527,472 A | 6/1996 | Bellottl et al. |
| 5,536,413 A | 7/1996 | Bormann et al. |
| 5,540,841 A | 7/1996 | Gsell et al. |
| 5,543,060 A | 8/1996 | Pall et al. |
| 5,543,062 A * | 8/1996 | Nishimura ............ A61M 1/0209 210/257.1 |
| 5,547,576 A | 8/1996 | Onishi et al. |
| 5,547,591 A | 8/1996 | Hagihara et al. |
| 5,549,834 A | 8/1996 | Brown |
| 5,580,465 A | 12/1996 | Pall et al. |
| 5,587,070 A | 12/1996 | Pall et al. |
| 5,591,337 A | 1/1997 | Lynn et al. |
| 5,601,730 A | 2/1997 | Page et al. |
| 5,609,947 A | 3/1997 | Kamei et al. |
| 5,616,254 A | 4/1997 | Pall et al. |
| 5,632,906 A | 5/1997 | Ishida et al. |
| 5,637,271 A | 6/1997 | Suzuki et al. |
| 5,639,376 A | 6/1997 | Lee et al. |
| 5,649,903 A | 7/1997 | Deniega et al. |
| 5,660,731 A | 8/1997 | Piechocki et al. |
| 5,665,233 A | 9/1997 | Fukuda et al. |
| 5,670,060 A | 9/1997 | Matkovich et al. |
| 5,679,264 A | 10/1997 | Gsell |
| 5,690,815 A | 11/1997 | Krasnoff et al. |
| 5,695,653 A | 12/1997 | Gsell et al. |
| 5,707,520 A | 1/1998 | Kuroki et al. |
| 5,738,796 A | 4/1998 | Bormann et al. |
| 5,744,047 A | 4/1998 | Gsell et al. |
| 5,769,839 A | 6/1998 | Carmen et al. |
| 5,772,880 A | 6/1998 | Lynn et al. |
| 5,779,902 A | 7/1998 | Zuk, Jr. |
| 5,788,661 A | 8/1998 | Japuntich |
| 5,795,483 A | 8/1998 | Ung-Chhun et al. |
| 5,798,041 A | 8/1998 | Zuk, Jr. |
| 5,804,280 A | 9/1998 | Pall et al. |
| 5,817,237 A | 10/1998 | Lee et al. |
| 5,820,755 A | 10/1998 | Kraus et al. |
| 5,836,934 A | 11/1998 | Beshel |
| 5,837,140 A | 11/1998 | Flni et al. |
| 5,885,457 A | 3/1999 | Breillatt, Jr. et al. |
| 5,895,575 A | 4/1999 | Kraus et al. |
| 5,902,490 A | 5/1999 | Zuk, Jr. |
| 5,935,436 A | 8/1999 | Lee et al. |
| 5,938,940 A | 8/1999 | Zuk, Jr. |
| 5,951,877 A | 9/1999 | Langley et al. |
| 5,954,971 A | 9/1999 | Pages et al. |
| 5,989,441 A | 11/1999 | Rashldbaigi et al. |
| 5,997,496 A | 12/1999 | Sekignchi et al. |
| 6,010,633 A | 1/2000 | Zuk, Jr. et al. |
| 6,013,184 A | 1/2000 | Fukuda et al. |
| 6,015,500 A | 1/2000 | Zuk, Jr. |
| 6,022,306 A | 2/2000 | Dumont et al. |
| 6,030,539 A | 2/2000 | Zuk, Jr. |
| 6,032,807 A | 3/2000 | Sternberg et al. |
| 6,048,464 A | 4/2000 | Tanaka et al. |
| 6,051,136 A | 4/2000 | Mari |
| 6,053,856 A | 4/2000 | Hlavinka |
| 6,053,885 A | 4/2000 | Beshel |
| 6,074,869 A | 6/2000 | Pall et al. |
| 6,080,322 A | 6/2000 | Deniega et al. |

(56) References Cited

U.S. PATENT DOCUMENTS

| | | | |
|---|---|---|---|
| 6,083,584 A | 7/2000 | Smith et al. |
| 6,086,770 A | 7/2000 | Matkovich |
| 6,102,883 A | 8/2000 | Kingsley et al. |
| 6,123,859 A | 9/2000 | Lee et al. |
| 6,129,853 A | 10/2000 | Sasayama et al. |
| 6,139,757 A | 10/2000 | Ohmura et al. |
| 6,159,375 A | 12/2000 | Lee et al. |
| 6,168,718 B1 | 1/2001 | Sutter et al. |
| 6,189,704 B1 | 2/2001 | Dennehey et al. |
| 6,197,207 B1 | 3/2001 | Chapman et al. |
| 6,200,287 B1 | 3/2001 | Keller et al. |
| 6,221,264 B1 | 4/2001 | Ishida et al. |
| 6,231,770 B1 | 5/2001 | Bormann et al. |
| 6,251,276 B1 | 6/2001 | Motomura |
| 6,251,284 B1 | 6/2001 | Bischof et al. |
| 6,267,898 B1 | 7/2001 | Fukuda et al. |
| 6,267,926 B1 | 7/2001 | Reed et al. |
| 6,274,055 B1 | 8/2001 | Zuk, Jr. |
| 6,322,604 B1 | 11/2001 | Midkiff |
| 6,325,422 B1 | 12/2001 | Verkaart et al. |
| 6,336,916 B1 | 1/2002 | Bormann et al. |
| 6,337,026 B1 | 1/2002 | Lee et al. |
| 6,348,156 B1 | 2/2002 | Vishnci et al. |
| 6,352,642 B1 | 3/2002 | Fukuda et al. |
| 6,355,174 B1 | 3/2002 | Robertson |
| 6,358,420 B2 | 3/2002 | Blickhan et al. |
| 6,428,712 B1 | 8/2002 | Castino |
| 6,488,860 B2 | 12/2002 | Mari et al. |
| 6,495,039 B1 | 12/2002 | Lee et al. |
| 6,497,685 B1 | 12/2002 | Dennehey et al. |
| 6,497,821 B1 | 12/2002 | Bellamy, Jr. et al. |
| 6,523,698 B1 | 2/2003 | Dennehey et al. |
| 6,527,957 B1 | 3/2003 | Deniega et al. |
| 6,565,782 B1 | 5/2003 | Wang et al. |
| D475,787 S | 6/2003 | Zia et al. |
| 6,592,507 B2 | 7/2003 | Jorgensen et al. |
| 6,592,613 B1 | 7/2003 | Ishida et al. |
| 6,602,812 B1 | 8/2003 | Onodera et al. |
| 6,629,613 B1 | 10/2003 | Kraus et al. |
| 6,645,388 B2 | 11/2003 | Sheikh-Ali |
| 6,660,171 B2 | 12/2003 | Zuk, Jr. |
| 6,663,586 B2 | 12/2003 | Verkaart et al. |
| 6,670,128 B2 | 12/2003 | Smith et al. |
| 6,688,476 B2 * | 2/2004 | Breillatt, Jr. ......... A61M 1/3633 210/232 |
| 6,688,935 B1 | 2/2004 | Lin |
| 6,695,805 B1 | 2/2004 | Sun et al. |
| 6,699,388 B1 | 3/2004 | Iwamoto et al. |
| 6,709,412 B2 | 3/2004 | Vandlik et al. |
| 6,723,062 B1 | 4/2004 | Westberg et al. |
| 6,723,238 B2 | 4/2004 | Romanavskas et al. |
| 6,730,054 B2 | 5/2004 | Pierce et al. |
| 6,730,055 B2 | 5/2004 | Bainbridge et al. |
| 6,740,239 B2 | 5/2004 | Hogberg et al. |
| 6,746,841 B1 | 6/2004 | Fomovskaia et al. |
| 6,767,466 B2 | 7/2004 | Kraus et al. |
| 6,773,413 B2 | 8/2004 | Keller et al. |
| 6,796,954 B2 | 9/2004 | Sawamoto et al. |
| 6,824,688 B2 | 11/2004 | Breillatt, Jr. et al. |
| 6,872,307 B2 | 3/2005 | Bischof |
| 6,875,191 B2 | 4/2005 | Smith et al. |
| 6,939,468 B2 | 9/2005 | Wang et al. |
| 6,945,411 B1 | 9/2005 | Bormann et al. |
| 6,955,700 B2 | 10/2005 | Zia et al. |
| 6,960,179 B2 | 11/2005 | Gura |
| 6,964,646 B1 | 11/2005 | Biesel |
| 6,977,044 B1 | 12/2005 | Oishi et al. |
| 6,994,790 B2 | 2/2006 | Corbin, III et al. |
| 6,997,893 B2 | 2/2006 | Mathias et al. |
| 7,011,761 B2 | 3/2006 | Muller |
| 7,025,881 B2 | 4/2006 | Heim |
| 7,041,076 B1 | 5/2006 | Westberg et al. |
| 7,052,606 B2 | 5/2006 | Gibbs et al. |
| 7,059,429 B2 | 6/2006 | Taylor et al. |
| 7,060,183 B1 | 6/2006 | Goudaliez et al. |
| 7,083,697 B2 | 8/2006 | Dao et al. |
| 7,125,493 B2 | 10/2006 | Wang et al. |
| 7,140,497 B2 | 11/2006 | Verpoort et al. |
| 7,144,496 B2 | 12/2006 | Meserol et al. |
| 7,156,240 B2 | 1/2007 | Oishi et al. |
| 7,169,547 B2 | 1/2007 | Rubinstein et al. |
| 7,182,865 B2 | 2/2007 | Latza |
| 7,186,231 B2 | 3/2007 | Takagi et al. |
| 7,217,365 B2 | 5/2007 | Fukuda et al. |
| 7,241,281 B2 | 7/2007 | Coelho et al. |
| 7,264,608 B2 | 9/2007 | Bischof et al. |
| 7,270,757 B1 | 9/2007 | Zuk, Jr. |
| 7,278,541 B2 | 10/2007 | Breillatt, Jr. et al. |
| 7,281,632 B2 | 10/2007 | Zia |
| 7,303,605 B2 | 12/2007 | Zia et al. |
| 7,332,096 B2 | 2/2008 | Blickhan |
| 7,351,344 B2 | 4/2008 | Verri et al. |
| 7,353,956 B2 | 4/2008 | Lynn et al. |
| 7,357,897 B2 | 4/2008 | Smith et al. |
| 7,361,277 B2 | 4/2008 | Bormann et al. |
| 7,374,870 B2 | 5/2008 | Herman et al. |
| 7,393,628 B2 | 7/2008 | Wagner et al. |
| 7,410,066 B2 | 8/2008 | Yamada et al. |
| 7,424,821 B1 | 9/2008 | Benjamin et al. |
| 7,438,821 B2 | 10/2008 | Yokomizo et al. |
| 7,439,013 B2 | 10/2008 | Kuno et al. |
| 7,445,124 B2 | 11/2008 | Cavallini et al. |
| 7,488,302 B1 | 2/2009 | Helm et al. |
| 7,517,333 B2 | 4/2009 | Vandlik et al. |
| 7,524,425 B2 | 4/2009 | Mari et al. |
| 7,531,098 B2 | 5/2009 | Robinson et al. |
| 7,534,348 B2 | 5/2009 | Reitz et al. |
| 7,566,315 B2 | 7/2009 | Hirabuki |
| 7,569,026 B2 | 8/2009 | Sugawara |
| 7,591,954 B2 | 9/2009 | Kimura et al. |
| 7,592,134 B2 | 9/2009 | Sato et al. |
| 7,597,677 B2 | 10/2009 | Gura et al. |
| 7,597,806 B2 | 10/2009 | Uchi et al. |
| 7,601,268 B2 | 10/2009 | Ragusa |
| 7,625,351 B2 | 12/2009 | Messier |
| 7,641,794 B2 | 1/2010 | Oka et al. |
| 7,648,452 B2 | 1/2010 | Holmes et al. |
| 7,651,474 B2 | 1/2010 | Van Waeg et al. |
| 7,655,146 B2 | 2/2010 | Ozeki et al. |
| 7,682,329 B2 | 3/2010 | Gibbs et al. |
| 7,686,779 B1 | 3/2010 | Gibbs |
| 7,686,797 B2 | 3/2010 | Zia et al. |
| 7,695,423 B2 | 4/2010 | Robinson et al. |
| 7,695,627 B2 | 4/2010 | Bosch et al. |
| 7,721,898 B2 | 5/2010 | Yagi et al. |
| 7,736,516 B2 | 6/2010 | Zambianchi et al. |
| 7,775,376 B2 | 8/2010 | Bonaguidi et al. |
| 7,789,245 B2 | 9/2010 | Westberg et al. |
| 7,789,847 B2 | 9/2010 | Gibbs et al. |
| 7,790,039 B2 | 9/2010 | Bosch et al. |
| 7,793,787 B2 | 9/2010 | Mizomoto et al. |
| 7,819,793 B2 | 10/2010 | Lindell et al. |
| 7,820,371 B2 | 10/2010 | Onodera et al. |
| 7,854,845 B2 | 12/2010 | Zuk, Jr. |
| 7,896,830 B2 | 3/2011 | Gura et al. |
| 7,897,038 B2 | 3/2011 | Zia |
| 7,910,008 B2 | 3/2011 | Sommer et al. |
| 7,943,372 B2 | 5/2011 | Olivier |
| 7,985,337 B2 | 7/2011 | Heuser et al. |
| 7,993,531 B2 | 8/2011 | Oleskiewicz et al. |
| 7,993,847 B2 | 8/2011 | Togawa et al. |
| 8,052,632 B2 | 11/2011 | Ghelli et al. |
| 8,052,667 B2 | 11/2011 | Rosiello et al. |
| 8,057,377 B2 | 11/2011 | Holmes et al. |
| 8,057,670 B2 | 11/2011 | Zia et al. |
| 8,057,672 B2 | 11/2011 | Chung et al. |
| 8,123,940 B2 | 2/2012 | Sumian et al. |
| 8,136,676 B2 | 3/2012 | Mizomoto et al. |
| RE43,310 E | 4/2012 | Ishida et al. |
| 8,173,027 B2 | 5/2012 | Hogberg et al. |
| 8,206,331 B2 | 6/2012 | Gura et al. |
| 8,236,184 B2 | 8/2012 | Holmes et al. |
| 8,262,640 B2 | 9/2012 | Zia et al. |
| 8,277,406 B2 | 10/2012 | Felt et al. |

(56) References Cited

U.S. PATENT DOCUMENTS

| | | |
|---|---|---|
| 8,287,742 B2 | 10/2012 | Holmes |
| 8,288,116 B2 | 10/2012 | Chen |
| 8,336,717 B2 | 12/2012 | Zia |
| 8,337,700 B1 | 12/2012 | Zuk, Jr. |
| 8,349,254 B2 | 1/2013 | Hoshino |
| 8,361,320 B2 | 1/2013 | Zuk, Jr. |
| 8,409,316 B2 | 4/2013 | Nelson et al. |
| 8,425,448 B2 | 4/2013 | Felt et al. |
| 8,439,889 B2 | 5/2013 | Sano |
| 8,460,267 B2 | 6/2013 | Hirabuki |
| 8,486,174 B2 | 7/2013 | Gieseke et al. |
| 8,496,833 B2 | 7/2013 | Kobayashi |
| 8,501,008 B2 | 8/2013 | Lemke et al. |
| 8,517,967 B2 | 8/2013 | Rosiello et al. |
| 8,524,090 B2 | 9/2013 | Oka et al. |
| 8,540,879 B2 | 9/2013 | Heim |
| 8,541,538 B2 | 9/2013 | Nakao et al. |
| 8,551,375 B2 | 10/2013 | Brown et al. |
| 8,597,223 B2 | 12/2013 | Dumon D'Ayot et al. |
| 8,640,738 B2 | 2/2014 | Zia et al. |
| 2001/0027946 A1 | 10/2001 | Fukuda |
| 2002/0030002 A1 | 3/2002 | Verkaart |
| 2002/0053548 A1 | 5/2002 | Lee et al. |
| 2002/0058030 A1 | 5/2002 | Monroy et al. |
| 2003/0057147 A1 | 3/2003 | Sutcliffe et al. |
| 2003/0062299 A1 | 4/2003 | Lee et al. |
| 2003/0146150 A1 | 8/2003 | Hayashi |
| 2003/0150793 A1 | 8/2003 | Verpoort |
| 2003/0209479 A1 | 11/2003 | Lynn et al. |
| 2004/0077831 A1 | 4/2004 | Chapmann et al. |
| 2004/0142316 A1 | 7/2004 | Owen et al. |
| 2004/0178140 A1 | 9/2004 | Bell et al. |
| 2004/0251195 A1 | 12/2004 | Oka et al. |
| 2005/0137517 A1 | 6/2005 | Blickhan et al. |
| 2005/0148748 A1 | 7/2005 | Tanaka et al. |
| 2005/0252821 A1 | 11/2005 | Azzolini et al. |
| 2005/0287124 A1 | 12/2005 | Watanabe et al. |
| 2006/0016753 A1 | 1/2006 | Sowemino-Coker et al. |
| 2006/0054557 A1 | 3/2006 | Hori et al. |
| 2006/0086666 A1 | 4/2006 | Mari et al. |
| 2006/0086675 A1 | 4/2006 | Purdum et al. |
| 2006/0108272 A1 | 5/2006 | Ariagno et al. |
| 2006/0128016 A1 | 6/2006 | Tokushima et al. |
| 2006/0180526 A1 | 8/2006 | Sugawara et al. |
| 2006/0180542 A1 | 8/2006 | Mari et al. |
| 2006/0226090 A1 | 10/2006 | Robinson et al. |
| 2006/0234210 A1 | 10/2006 | Kenan et al. |
| 2007/0029256 A1 | 2/2007 | Nakano et al. |
| 2007/0095764 A1 | 5/2007 | Yang et al. |
| 2007/0118063 A1 | 5/2007 | Gibbs et al. |
| 2007/0119780 A1 | 5/2007 | Zia et al. |
| 2007/0175816 A1 | 8/2007 | Verpoort |
| 2007/0212674 A1 | 9/2007 | Spiers et al. |
| 2008/0011691 A1 | 1/2008 | Yamada et al. |
| 2008/0023394 A1 | 1/2008 | Naruse et al. |
| 2008/0050275 A1 | 2/2008 | Bischof et al. |
| 2008/0073294 A1 | 3/2008 | Zambianchi et al. |
| 2008/0110829 A1 | 5/2008 | Kobayashi et al. |
| 2008/0147240 A1 | 5/2008 | Kobayashi et al. |
| 2008/0156728 A1 | 7/2008 | Blickhan et al. |
| 2008/0223798 A1 | 9/2008 | Paretta et al. |
| 2008/0260710 A1 | 10/2008 | Kusunoki et al. |
| 2009/0036322 A1 | 2/2009 | Bradley et al. |
| 2009/0071905 A1 | 3/2009 | Goudaliez et al. |
| 2009/0159522 A1 | 6/2009 | Marmey et al. |
| 2009/0173685 A1* | 7/2009 | Imai ............... A61M 1/3633 210/243 |
| 2009/0194489 A1 | 8/2009 | Vandlik et al. |
| 2009/0272701 A1 | 11/2009 | Holmes et al. |
| 2009/0324567 A1 | 12/2009 | Spiers et al. |
| 2010/0025335 A1 | 2/2010 | Shimagaki et al. |
| 2010/0062412 A1 | 3/2010 | Nirasawa et al. |
| 2010/0081985 A1 | 4/2010 | Pittinger et al. |
| 2010/0084332 A1 | 4/2010 | Lynn et al. |
| 2010/0108596 A1 | 5/2010 | Duhaut et al. |
| 2010/0136677 A1 | 6/2010 | Delaronde-Wilton et al. |
| 2010/0270232 A1 | 10/2010 | Iwanaga et al. |
| 2010/0291629 A1 | 11/2010 | Fournier-Wirth et al. |
| 2011/0031191 A1 | 2/2011 | Fukuda et al. |
| 2011/0136096 A1 | 6/2011 | Hassanein et al. |
| 2011/0152740 A1 | 6/2011 | Gibbs et al. |
| 2011/0192798 A1 | 8/2011 | Goudaliez et al. |
| 2011/0238029 A1 | 9/2011 | Biset et al. |
| 2011/0240549 A1 | 10/2011 | Andou et al. |
| 2012/0015794 A1 | 1/2012 | Holmes et al. |
| 2012/0024779 A1 | 2/2012 | Ochiai et al. |
| 2012/0067810 A1 | 3/2012 | Yokomizo et al. |
| 2012/0067811 A1 | 3/2012 | Yokomizo et al. |
| 2012/0111807 A1 | 5/2012 | Hillyer et al. |
| 2012/0115124 A1 | 5/2012 | Yoshida et al. |
| 2012/0135391 A1 | 5/2012 | Shaz et al. |
| 2012/0141975 A1 | 6/2012 | Sato et al. |
| 2012/0160763 A1 | 6/2012 | Yokomizo et al. |
| 2012/0160782 A1 | 6/2012 | Yokomizo et al. |
| 2012/0165176 A1 | 6/2012 | Andou et al. |
| 2012/0171658 A1 | 7/2012 | Bein et al. |
| 2012/0175313 A1 | 7/2012 | Barry et al. |
| 2012/0175319 A1 | 7/2012 | Cotton et al. |
| 2012/0228207 A1 | 9/2012 | Mathias et al. |
| 2012/0258459 A1 | 10/2012 | Huang et al. |
| 2012/0263771 A1 | 10/2012 | Carlson et al. |
| 2012/0269679 A1 | 10/2012 | Payrat et al. |
| 2012/0289926 A1 | 11/2012 | Hirabuki et al. |
| 2012/0294826 A1 | 11/2012 | Spitalnik et al. |
| 2012/0315664 A1 | 12/2012 | Friedrich et al. |
| 2013/0001149 A1 | 1/2013 | Yamamoto et al. |
| 2013/0004937 A1 | 1/2013 | Yoshida et al. |
| 2013/0005557 A1 | 1/2013 | Yokomizo et al. |
| 2013/0005558 A1 | 1/2013 | Inadome et al. |
| 2013/0046225 A1 | 2/2013 | Nose et al. |
| 2013/0047861 A1 | 2/2013 | Yoshida et al. |
| 2013/0092319 A1 | 4/2013 | Lynn et al. |
| 2013/0140228 A1 | 6/2013 | Schwender et al. |
| 2013/0150793 A1 | 6/2013 | Beissel et al. |
| 2013/0153482 A1 | 6/2013 | Gibbs et al. |
| 2013/0264288 A1 | 10/2013 | Hlavinka et al. |
| 2013/0323711 A1 | 12/2013 | Singh et al. |
| 2013/0345674 A1 | 12/2013 | Kusters et al. |

FOREIGN PATENT DOCUMENTS

| | | |
|---|---|---|
| DE | 37 34 170 A1 | 4/1989 |
| DE | 40 19 114 A1 | 10/1991 |
| DE | 40 22 700 A1 | 1/1992 |
| DE | 93 11 251 U1 | 10/1993 |
| DE | 43 41 005 A1 | 6/1995 |
| DE | 296 03 873 U1 | 6/1996 |
| DE | 197 33 407 A1 | 2/1999 |
| DE | 102 39 658 A1 | 11/2003 |
| DE | 103 15 484 A1 | 8/2004 |
| EP | 0 370 584 A1 | 5/1990 |
| EP | 0 406 485 A1 | 1/1991 |
| EP | 0 408 462 B1 | 1/1991 |
| EP | 0 516 846 A1 | 12/1992 |
| EP | 0 526 678 A1 | 2/1993 |
| EP | 0 573 405 A1 | 12/1993 |
| EP | 0 606 646 B1 | 9/1997 |
| EP | 0 792 677 A1 | 9/1997 |
| EP | 0958838 A2 | 11/1999 |
| EP | 0 728 491 B1 | 11/2000 |
| EP | 1 048 305 A2 | 11/2000 |
| EP | 0 888 789 B1 | 9/2002 |
| EP | 1300128 A1 | 4/2003 |
| EP | 1300168 A1 | 4/2003 |
| EP | 1 484 390 A1 | 12/2004 |
| EP | 1 611 907 A1 | 1/2006 |
| EP | 0 933 090 B1 | 7/2006 |
| EP | 1 897 571 A1 | 3/2008 |
| EP | 1 902 740 A1 | 3/2008 |
| EP | 0 976 413 B1 | 4/2008 |
| EP | 1 925 328 A2 | 5/2008 |
| EP | 0 953 361 B1 | 2/2013 |
| EP | 1 838 412 B1 | 5/2013 |
| FR | 2 821 762 A1 | 9/2002 |

(56) References Cited

FOREIGN PATENT DOCUMENTS

| | | | |
|---|---|---|---|
| GB | 1300850 A | 12/1972 |
| GB | 1302564 A | 1/1973 |
| GB | 2473621 A | 3/2011 |
| IE | 2009/0703 | 6/2011 |
| WO | WO 88/002264 A1 | 4/1988 |
| WO | WO 89/002304 A1 | 3/1989 |
| WO | WO 90/000059 A1 | 1/1990 |
| WO | WO 95/000631 A1 | 1/1995 |
| WO | WO 95/017234 A1 | 6/1995 |
| WO | WO 98/028057 A1 | 7/1998 |
| WO | WO 99/013925 A1 | 3/1999 |
| WO | WO 99/016480 A1 | 4/1999 |
| WO | WO 99/039758 A1 | 8/1999 |
| WO | WO 99/044718 A1 | 9/1999 |
| WO | WO 99/053975 A1 | 10/1999 |
| WO | WO 00/020053 A1 | 4/2000 |
| WO | WO 00/053287 A1 | 9/2000 |
| WO | WO 00/054824 A1 | 9/2000 |
| WO | WO 00/062840 A1 | 10/2000 |
| WO | WO 01/032828 A2 | 5/2001 |
| WO | WO 01/036022 A1 | 5/2001 |
| WO | WO 02/011855 A1 | 2/2002 |
| WO | WO 02/024256 A1 | 3/2002 |
| WO | WO 03/047655 A1 | 6/2003 |
| WO | WO 06/003350 A1 | 1/2006 |
| WO | WO 07/025738 A2 | 3/2007 |
| WO | WO 07/054638 A1 | 5/2007 |
| WO | WO 08/092610 A1 | 8/2008 |
| WO | WO 08/103142 A1 | 8/2008 |
| WO | WO 09/005046 A1 | 1/2009 |
| WO | WO 09/057574 A1 | 5/2009 |
| WO | WO 10/004104 A2 | 1/2010 |
| WO | WO 10/026891 A1 | 3/2010 |
| WO | WO 10/136447 A1 | 12/2010 |
| WO | WO 11/125617 A1 | 10/2011 |
| WO | WO 11/157822 A1 | 12/2011 |
| WO | WO 12/017291 A2 | 2/2012 |
| WO | WO 12/057029 A1 | 5/2012 |
| WO | WO 12/090834 A1 | 7/2012 |
| WO | WO 12/090835 A1 | 7/2012 |
| WO | WO 12/093179 A1 | 7/2012 |
| WO | WO 12/139209 A1 | 10/2012 |
| WO | WO 13/022491 | 2/2013 |

OTHER PUBLICATIONS

International Search Report and Written Opinion dated Nov. 26, 2014 for International Application No. PCT/US2014/041213.
Partial International Search Report dated Nov. 18, 2014 in PCT/IS2014/041210.
International Search Report and Written Opinion dated Feb. 5, 2015 in PCT/US2014/041210.
International Search Report for International Application No. PCT/US2014/041217 dated Mar. 23, 2015.

* cited by examiner

BIOLOGICAL FLUID FILTERS WITH MOLDED FRAME AND METHODS FOR MAKING SUCH FILTERS

FIELD OF THE DISCLOSURE

The present disclosure is directed to filters for the filtration of fluids such as, but not limited to, biological fluids and to methods of making such filters wherein at least the walls of the housing are made of a flexible material. More particularly, the present disclosure is directed to flexible housing filters that include one or more peripheral seals or, in the alternative, include a molded frame with flexible walls that capture the filter medium with no peripheral seals.

BACKGROUND

Using various manual and automated systems and methods, whole blood is collected and separated into its clinical components (typically red blood cells, platelets, and plasma). The collected components are typically individually stored and used to treat a variety of specific conditions and diseased states.

Before transfusing the collected blood components to a recipient in need of the components, or before subjecting blood components to further treatment, it is often desirable to minimize the presence of impurities or other materials that may cause undesired side effects in the recipient. For example, because of possible reactions, it is generally considered desirable to reduce the number of leukocytes in blood components before storage, or at least before transfusion (i.e., "leukoreduction").

Filters are widely used to accomplish leukoreduction in blood products today (e.g., filtration of leukocytes from whole blood, red cells, and/or platelet products). Filters typically include a filter media disposed between mating and/or opposed walls of a filter housing. Inlet and outlet ports associated with the housing provide flow to and from the interior of the filter. Traditionally, the walls of the filter housing have been made of a rigid, typically polymeric, material. More recently, filters wherein at least the walls of the housing are made of a flexible material have been used in blood collection kits. Soft or flexible housing filters provide the advantage of being able to withstand handling and centrifuging without breakage of the filter. Examples of soft housing filters are disclosed in U.S. Pat. No. 6,367,634; U.S. Pat. No. 6,422,397; U.S. Pat. No. 6,745,902; U.S. Pat. No. 7,353,956; U.S. Pat. No. 7,332,096; U.S. Pat. No. 7,278,541; and U.S. Patent Application Publication No. 2003/0209479, all of which are hereby incorporated by reference herein.

While flexible housing filters are now commonly used in the field of blood processing, there exists an ongoing desire to improve the construction, performance, and manufacturability of such filters.

SUMMARY

In one aspect, the present disclosure is directed to a biological fluid filter assembly that includes a molded frame with a rim defining a central opening. The molded frame includes an inner surface and an outer surface and an inlet side and an outlet side with a filter medium including a plurality of stacked sheets captured within the frame. The filter assembly further includes a pair of flexible housing walls, one of which is on the inlet side and the other is on the outlet side. The filter assembly further includes an inlet port associated with the inlet side of the filter assembly and an outlet port associated with the outlet side of the filter assembly.

In a further aspect, the present disclosure is directed to a method for making a flexible-walled housing filter. The method includes locating a filter medium defining an outer peripheral edge and having an inlet side and an outlet side in a cavity of a molding apparatus. The method further includes introducing a molten polymeric material into said cavity to form a frame around said peripheral edge of said filter medium, the frame defining a pair of central openings at said inlet and outlet sides of said medium. The method further includes locating a flexible housing wall at a surface of the molded frame at the inlet side and locating a flexible housing wall to another surface of the molded frame at said outlet side.

BRIEF DESCRIPTION OF THE DRAWINGS

FIG. 29 (a)-(e) depicts the steps in a method of making a filter assembly in accordance with the present disclosure.

DETAILED DESCRIPTION OF THE EMBODIMENTS

Figure 1:
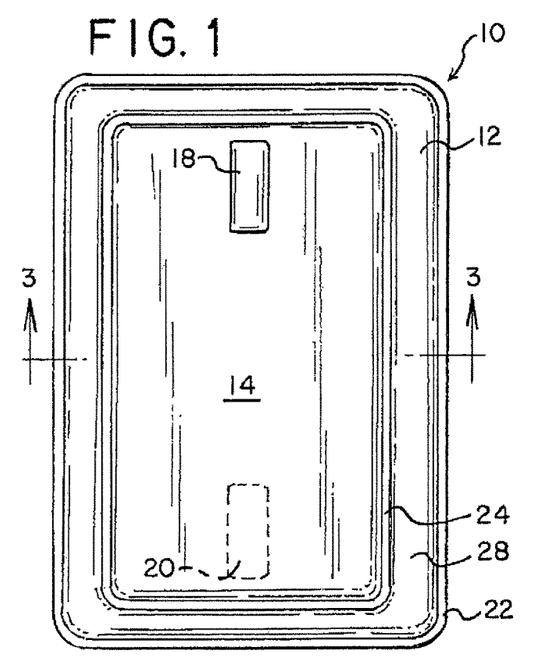
FIG. 1 is a plan view of a flexible housing filter assembly in accordance with the present disclosure.
Figure 2:
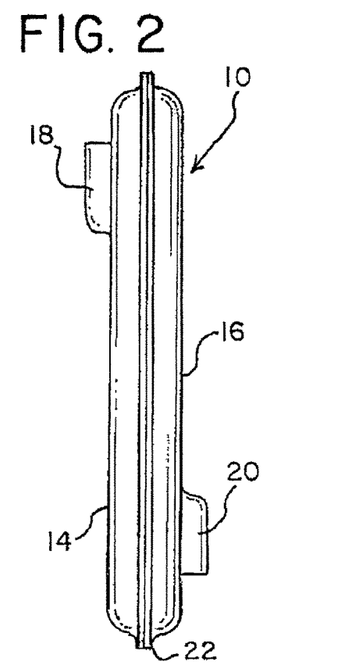
FIG. 2 is a side view of the flexible housing filter of FIG. 1.

The present disclosure is directed to a filter assembly 10 useful in the removal of selected components or compounds from a biological fluid, such as blood. As shown in FIGS. 1 and 2 and in accordance with the present disclosure, filter assembly 10 includes a housing 12 defined by a pair of outer housing walls 14 and 16. In one embodiment, housing walls 14 and 16 of housing 12 may be separate sheets of a flexible material such as, but not limited to, polyvinyl chloride or any other suitable material through which the biological fluid will not flow. The separate sheets may be sealed together along their peripheries as will be described in greater detail below. Alternatively, walls 14 and 16 may be provided from a single sheet of suitable flexible material folded over itself and sealed along the non-folded sides and/or end(s) of the facing panels. Still further, housing 12 may be provided as a pocket, sealed along three sides and open along one side through which the filter medium may be introduced, followed by the sealing of the remaining open end.

Figure 3:
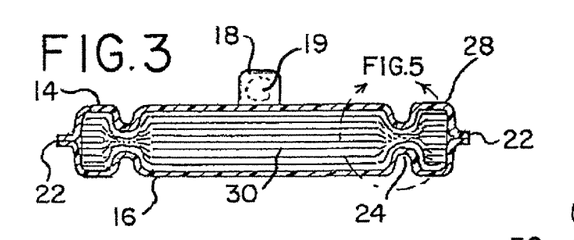
FIG. 3 is a cross-sectional end view taken along line 3-3 of the flexible housing filter of FIG. 1.

As shown in FIGS. 1 and 2, "inlet" housing wall 14 and "outlet" housing wall 16 include inlet port 18 and outlet port 20, respectively, positioned on opposite sides and near opposite ends of the filter assembly. Ports 18 and 20 need not be located near opposite ends of filter assembly 10 but may be positioned elsewhere, such as more centrally located and directly opposite each other. Ports 18 and 20 are adapted to receive other components of the fluid processing set such as tubing or the like. Inlet and outlet ports 18 and 20 may be secured to the associated walls 14 and 16 by any suitable means (e.g., being heat sealed thereto using radio frequency energy), or may be integrally molded with housing walls 14 and 16 as described in International Publication WO 00/62891, the contents of which are incorporated herein by reference. Ports 18 and 20 of the filter housing 12 are each preferably provided with an opening/aperture and an internal flow path 19, as shown in FIG. 3 (not shown in port 20) through which fluid flows into and out of filter assembly 10.

Figure 6:
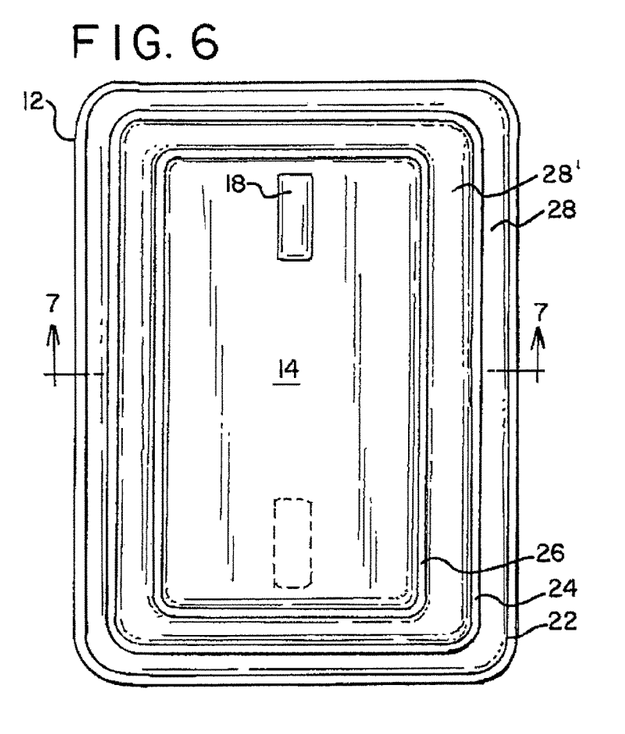
FIG. 6 is plan view of another embodiment of a flexible housing filter assembly in accordance with the present disclosure.
Figure 7:
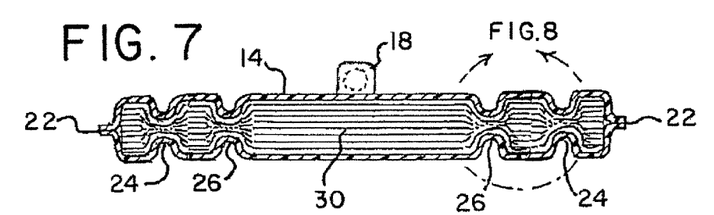
FIG. 7 is a cross-sectional end view taken along line 7-7 of the flexible housing filter of FIG. 6.
Figure 8:
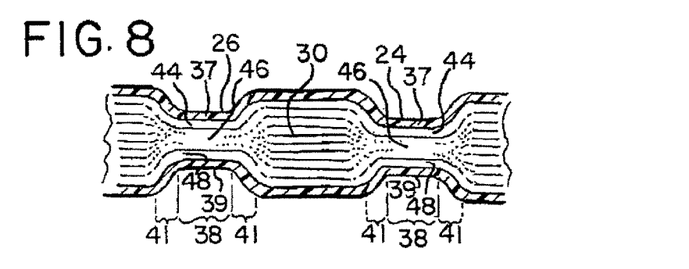
FIG. 8 is an enlarged cross-sectional view of the dual inner peripheral seal regions of the filter assembly shown in FIGS. 6-7.

As further shown in FIGS. 1 and 2, housing walls 14 and 16 are joined together at least substantially around their peripheries to form housing 12, and preferably entirely around their peripheries. In one embodiment, housing walls 14 and 16 are joined at their outermost peripheries with an outer peripheral seal 22. In addition, in accordance with the present disclosure, housing 12 may also include one or more "inner peripheral seals" 24 (and 26, as shown in FIGS. 6-8) spaced inwardly from outer peripheral seal 22. A gap 28 between outer peripheral seal 22 and inner seal 24 (or outer seal 22 and inner seals 24 and 26) provide(s) a cushioned periphery of the type described in U.S. Patent Publication No. 2003/0209479, which is incorporated by reference herein in its entirety.

In one embodiment shown in FIG. 1, both outer seal 22 and inner seal 24 may have an at least substantially uniform width of greater than 6 mm and more preferably a width of between approximately 6-12, 6-10, or 6-8 mm. Gap 28 between outer 22 and inner 24 seals of FIG. 1 may be approximately 1-10, 1-8 or 1-6 mm. In the embodiment of FIG. 6, inner seal 24 may have a width of approximately 0.5-7, 0.7-5 or 1.0-4 mm. Outer seal 22 may have a width of greater than approximately 6 mm and more particularly approximately 6-12, 6-10 and 6-8 mm. Gap 28 and 28' between each of the adjacent seals may have a width of approximately 1-10, 1-8 or 1-6 mm.

Figure 9:
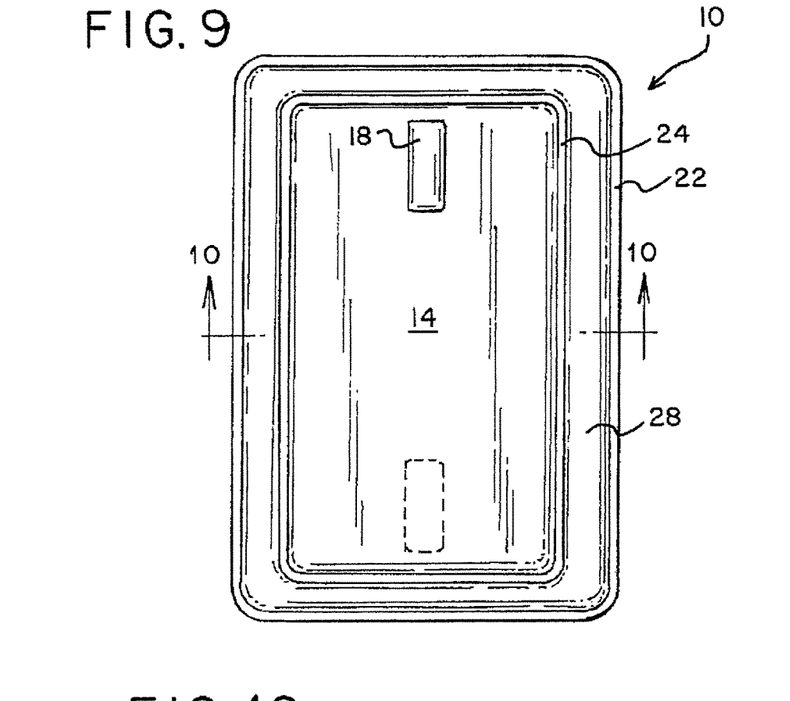
FIG. 9 is plan view of still another embodiment of a flexible housing filter assembly in accordance with the present disclosure.
Figure 10:
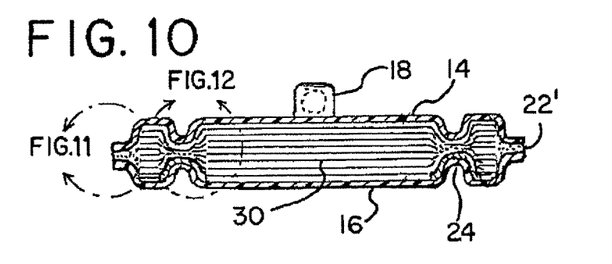
FIG. 10 is a cross-sectional end view taken along line 10-10 of the flexible housing filter assembly of FIG. 9.

With respect to the embodiment of FIG. 9 (discussed in more detail below) inner seal 24 may have a seal width of approximately 0.5-7, 0.7-5, 1.0-4 mm and outer seal 22 may have a seal width of greater than 6 mm and more particularly 6-12, 6-10 or 6-8 mm. Gap 28 between the inner and outer seals may have a width of approximately 1-10, 1-8 and 1-6 mm.

As shown in FIGS. 3-4, 7, 10, 14-16 filter assemblies of the type disclosed herein further include a filter medium 30 that is captured between housing walls 14 and 16. Filter medium 30 may include one or more sheets of one or more materials capable of removing selected components, compounds, or other particulates from the biological fluid. In one embodiment, filter medium 30 is specifically suited for the removal of at least leukocytes from blood. The one or more sheets of filter material may be made of any suitable biocompatible, medical grade material with pores sized to remove the selected components, compounds or other particulates. The one or more sheets of filter medium may be provided as a mesh, a woven fiber, a melt-blown, non-woven fibrous material or other suitable porous structure.

In one embodiment, filter medium 30 may include a plurality of sheets, such as, for example, a plurality of melt-blown, non-woven fibrous sheets. In a further embodiment, filter medium 30 may be provided as a pad or stack of a plurality of filter sheets, as shown in FIG. 3 and more particularly, in FIG. 4.

Figure 4:
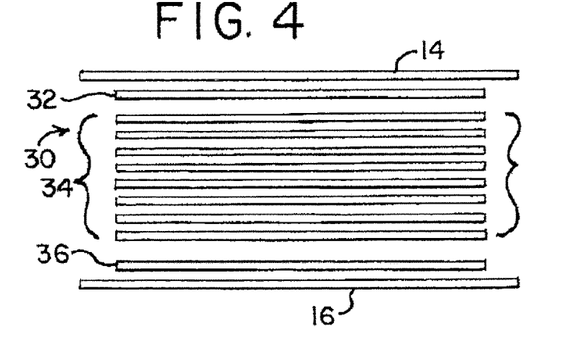
FIG. 4 is an exploded view of a filter assembly in accordance with the present disclosure.

As shown in FIG. 4, a filter pad or stack of filter medium 30 may include a plurality of individual sheets, one or more of which define at least first, second and third elements or regions that are suited for the selective removal of components, or compounds, or particulates and/or to provide other functions to filter assembly 10. For example, as shown in FIG. 4, filter medium 30 may include at least a first element or region 32, a second element or region 34, and a third element or region 36. The stack of sheets that includes elements 32, 34, 36 is captured between housing walls 14 and 16 and sealed in the manner described above.

Thus, for example, as further shown in FIG. 4, first element or region 32 may preferably be adjacent to inlet housing wall 14. Although shown as a single sheet in FIG. 4, it will be understood that the first element or region 32 may include one or more sheets of a selected filtration material. The first element may be referred to as "pre-filter" and may be particularly well suited for the removal of microaggregates.

Continuing with a description of the elements or regions that make up filter medium 30 in the direction of flow from the inlet housing wall 14 toward the outlet housing wall 16, a second element or region 34 is located downstream of first element 32. As shown in FIG. 4, second element 34 may include one or more sheets of a filter material of the type described above that is capable of removing certain blood components, such as leukocytes. Typically, element 34 may include a plurality of sheets, most typically between 2 and 50 individual sheets each preferably made of a melt-blown, non-woven fibrous material. Continuing in the downstream direction from second element 34 is a third element 36 that is located between the second element and the adjacent outlet housing wall 16. The first, second and third elements 32, 34 and 36 will now be described in greater detail.

As noted above, first element 32 may be considered a "pre-filter" for filtering out certain larger-sized particles and components. Element 32 is preferably made of any suitable biocompatible material with pores sufficiently sized to remove or retain certain particles, such as microaggregates, while allowing other components, such as leukocytes, to substantially pass. In one embodiment, the material(s) used for the sheet(s) that make up first element or region 32 may be polybutyleneterephthalate (PBT), polyethyleneterephthalate (PET), or polypropylene. In an embodiment, the overall thickness of first element 32 (in the unsealed areas of filter medium 30) may be approximately 0.127-1.106 mm. More particularly, the thickness of first element 32 may be approximately 0.305-0.711 mm and even more particularly approximately 0.432-0.559 mm.

Second element or region 34 may provide the filtration region of filter medium 30 that is primarily responsible for the removal of blood cells. Thus, second element 34 may typically be made of a biocompatible material with pores sized to retain leukocytes, i.e., white blood cells. Materials suitable for use as the second element 34 include the PBT, PET and PP materials described above in connection with first element 32. Second element 34 may have a thickness in the unsealed areas of the medium of approximately 0.254-15.24 mm, or more particularly, approximately 5.08-12.7 mm, and even more particularly approximately 7.11-8.9 mm.

Figures 13, 14, 15, 16:
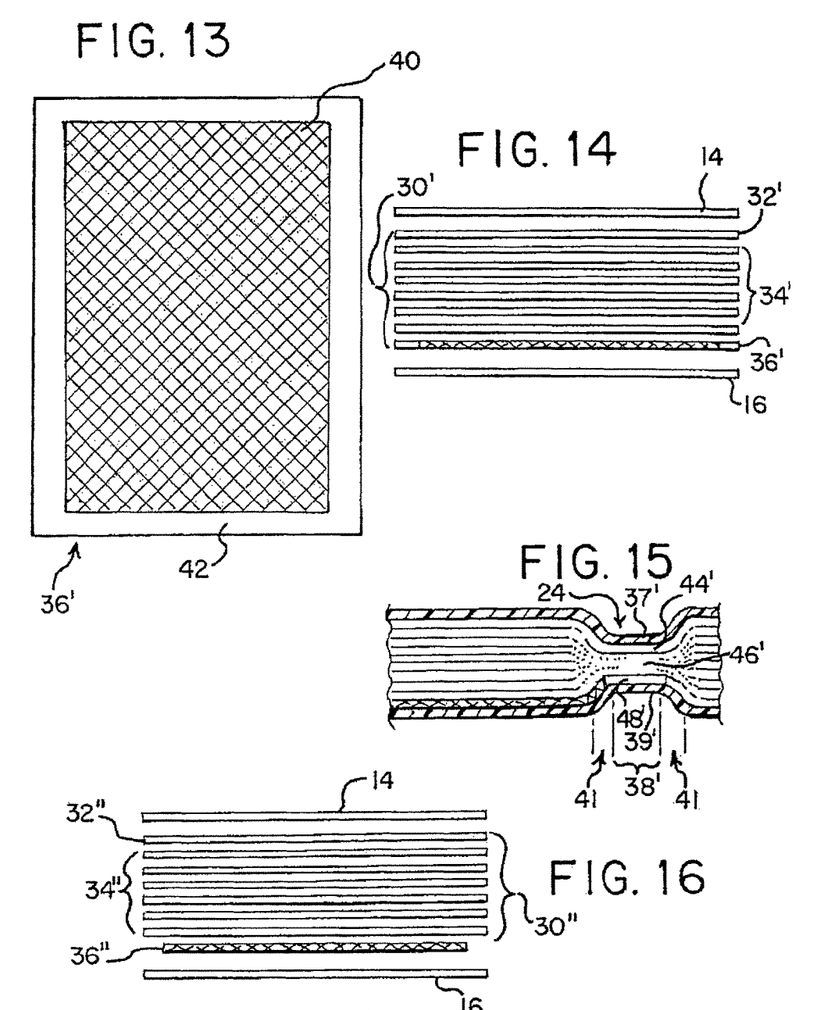
FIG. 13 is a plan view of one embodiment of the third element of the filter assembly of any one of the previous embodiments.
FIG. 14 is an exploded view of the housing walls and first, second and third filter elements including the third element of FIG. 13.
FIG. 15 is a partial, cross-sectional view of an inner peripheral seal of the embodiment of the filter assembly of FIGS. 13-14.
FIG. 16 is an exploded view of the housing walls, first, second and third filter elements and an alternative embodiment of the third element of FIGS. 13-14.
Figure 17:
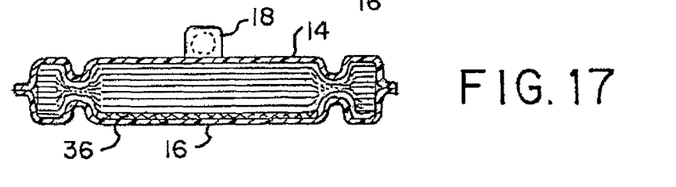
FIG. 17 is a cross-sectional end view of a filter assembly including the embodiment of the third element as shown in FIG. 16.

Third element or region 36 (sometimes referred to as the "post-filter") may likewise be made of a suitable biocompatible porous material that allows for the filtrate to pass and exit through outlet port 20 in outlet housing wall 16. Third element 36 may further serve as a manifold or support and spacing structure between housing wall 16 and filter medium 30. Third element 36 may be made of any organic or inorganic material and may be a mesh, a woven fibrous structure, or a melt-blown, non-woven fibrous structure. The thickness of third element 36 in the unsealed areas of filter medium 30 is preferably less than 0.04 cm or greater than 0.25 cm. In one embodiment, third element 36 may be a sheet that includes a mesh interior and, optionally, a non-mesh frame, as shown in FIG. 13 and described in greater detail below.

As discussed above and shown in FIGS. 1-12, filter assembly 10 and more specifically housing 12 of filter assembly 10 includes an outer peripheral seal 22 and one or more inner seals 24 (and, optionally, 26) inwardly spaced from outer peripheral seal 22. Both inner and outer seals 24 and 26 may be formed by any suitable means, such as pressure application, heat sealing and, preferably, radio frequency (RF) sealing.

Figure 5:
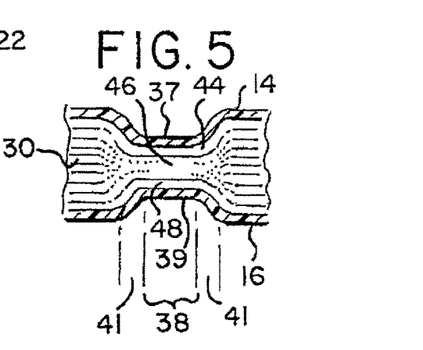
FIG. 5 is an enlarged cross-sectional view of an inner peripheral seal region of the filter assembly shown in FIGS. 1-4.
Figure 12:
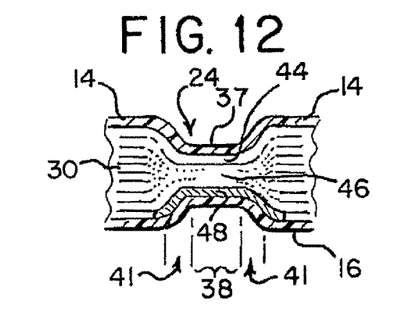
FIG. 12 is a partial an enlarged cross-sectional view of an inner seal region of the filter assembly shown in FIGS. 9-10.

In one embodiment, outer seal 22 may be formed strictly between the opposing housing walls 14 and 16. Inner seal 24, on the other hand, captures both housing walls 14 and 16 and the intervening elements or regions 32, 34 and 36 of filter medium 30 and the sheets thereof, as shown in FIGS. 5, 8 and 12. Thus, for example, inner seal 24 may include the housing material of housing walls 14, 16 and some or all of first, second and third elements described above. Where more than three elements are included in filter medium 30, inner seal 24 may likewise include material of some or all of such additional elements. Seals 22 and 24 (and 26) may be formed in a sequential process or in a simultaneous process. In addition, the elements of filter medium 30 may be sealed together first, followed by the sealing of housing walls 14 and 16 to the filter medium in a two-step process. Alternatively, the housing walls and filter medium 30 may be sealed altogether in a one-step process.

In accordance with the present disclosure, as a result of the applied pressure and RF energy, inner and outer seals 24, 26 and 22 define compressed areas that may include one or more differentiated or undifferentiated layers or bands within the seal. It will be understood that the inner seals 24 and/or 26 may themselves include a central section 38 of substantially uniform thickness between flared and less compressed peripheral sections 41, as shown in FIGS. 5, 8, 12 and 15. The thickness of the inner seals 24 and/or 26 and of the layers or bands within such seals described below are preferably an average of anywhere between 4-10 measurements taken within the central section 38 of the seal, as shown in FIGS. 5, 8 and 12, for example. Thus, in one embodiment, inner seals 24 and/or 26 may have a thickness of approximately 0.762-2.286 mm, more preferably approximately 1.02-2.032 mm and even more preferably approximately 1.27-1.778 mm.

In one embodiment, where housing walls 14 and 16 are sealed directly to each other at the outermost periphery, i.e., such outer seal 22 includes a single region 35 made up entirely of the material (for example, PVC) of housing walls 14 and 16. Inasmuch as inner seals 24 and/or 26 may include filter elements 32, 34 and 36, such inner seals 24 and 26 may include several layers or bands made up of the outer housing materials, materials of the filter medium 30 including the material of first, second and/or third filter elements, and composites or commingled layers thereof. Thus, in an embodiment where inner seal 24 and/or 26 includes the material(s) of the inner and outer housing wall 14 and 16 and the three filter elements 32, 34 and 36 (described above and shown in FIGS. 5, 8 and 12), seal 24 and/or 26 may include, in the direction of flow, a first layer 37 that includes entirely or at least substantially entirely the material of inlet housing wall 14. Using a scanning electron microscope, the post-seal thickness of such band 37 of the housing wall 14 may be approximately 0.076-0.381 mm or more particularly approximately 0.127-0.304 mm, or even more particularly 0.178-0.250 mm.

Adjacent to the first layer or band 37 and downstream therefrom is a second layer 44 that may be a composite of the housing material and the first and second elements or regions 32 and 34, described above and shown in FIG. 4. Composite layer 44 may have a post-seal thickness of approximately 0.1-0.5 mm, more particularly approximately 0.1-0.35 mm and even more particularly approximately 0.1-0.2 mm.

Downstream of layer 44 is preferably layer or band 46, which at least substantially includes the material of element 34 (i.e., the material(s) of the filter medium 30 for removing leukocytes). In accordance with the present disclosure, layer 46 may have a post-seal thickness of approximately 0.508-

1.27 mm or more particularly approximately 0.635-1.143 mm, or even more particularly approximately 0.762-0.9 mm.

Continuing with a description of the layers or bands within inner seals 24 and/or 26 (as measured within central section 38) and proceeding in the direction of flow and downstream of region 46 is region 48, which may be a composite of the material of housing wall and third filter element 36. The post seal thickness of layer 48 is less than 0.15 mm and more particularly approximately 0.001-0.12 mm and 0.01-0.08 mm. Finally, as further shown in FIGS. 5 and 8, layer 39 may include entirely or at least substantially entirely the material of outlet housing wall 16. The post-seal thickness of layer 39 may be approximately 0.254-0.406 mm, more particularly approximately 0.304-0.381 mm or approximately 0.330-0.3556 mm.

Figure 11:
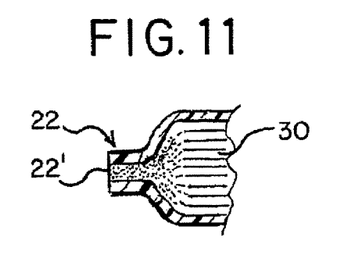
FIG. 11 is a partial, cross-sectional view of the outer peripheral seal of the filter assembly of FIGS. 9-10.

As described above, outer seal 22 may simply consist of the housing material of inlet and outlet walls 14, 16. In another embodiment, shown in FIGS. 9-12, outer seal 22 may also capture at least the first and second elements 32 and 34, respectively, as shown in FIG. 11. Thus, outer seal 22 includes, in the direction of flow, layers made up of the essentially housing material only having a thickness of approximately 0.076-0.381 mm, more particularly 0.127-0.304 mm, and even more particularly 0.178-0.25 mm. Following this region, there is a composite layer 22' that includes the housing material and the first and second regions, wherein the post-seal thickness of this composite layer is between approximately 0.076-0.762 mm, more particularly between 0.127-0.508 mm, and even more particularly between 0.178-0.381 mm. An RF die that includes a tear seal feature that also cuts and separates the now sealed filter assembly from the flexible housing sheets and filter media may be used. A smart generator may be particularly well-suited for such outer seal operation. (The thicknesses of the bands or layers within central section 38 of inner seals 24 and/or 26 may be as substantially described above.)

In another embodiment, as shown in FIGS. 13-17, the third element 36' may be a sheet with a central porous region 40, such as a mesh and an outer peripheral frame 42 integral with central porous region 40. As shown in FIG. 15, frame 42 or at least a portion of frame 42 may be captured within inner seal 24 and/or 26. In a further alternative, the mesh may be provided without a frame, wherein the peripheral portions of the all-mesh sheet may be captured within inner seal 24 and/or 26. In a further alternative, as depicted in FIG. 16, where the third element 36" is an all-mesh sheet without a frame, no part of the this third element is captured by inner seal 24 and/or 26. In this embodiment, third element or region 36" may be "free-floating" within filter assembly 10.

The material of the third element 36', 36" defines openings or voids through which filtered fluid passes before exiting the filter assembly 10 via the outlet port 20. The third element 36' (or 36") of FIG. 13 is shown with generally diamond-shaped openings or voids, but it is within the scope of the present disclosure for the openings or voids to be differently shaped (e.g., a regular shape, such as generally square or rectangular or circular or triangular or pentagonal or hexagonal, or an irregular shape). A primary purpose of the third element 36', 36" may be to act as a manifold which separates the filtration medium 34', 34" from the outlet side 16 of the filter housing, while allowing filtered fluid to freely flow from the filtration medium 34', 34" to outlet port 20. Accordingly, the voids in porous region 40 may be relatively large to provide third element 36', 36" with a porosity that is greater than the porosity of the filtration medium 34', 34". However, if the voids are too large, it is possible for the outlet side 14 of the filter housing to press against the filtration medium 34', 34" during use, thereby making it more difficult for filtered fluid to flow out of the filter assembly 10. Thus, it may be preferred for the third element 36', 36" to have an intermediate porosity, with voids that are large enough to allow substantially free flow of filtered fluid out of the filter assembly 10, but not so large as to negate the desired manifold effect. In one exemplary embodiment, the voids are generally rectangular or square or diamond-shaped, each having a height and width in the range of approximately 0.5-20 mm, with the third element 36', 36" having a thickness in the range of approximately 0.5-4 mm.

The porous region 40 of third element 36', 36" may have a generally uniform porosity or permeability, with generally uniform voids arranged in a uniform pattern, or may have a non-uniform porosity or permeability, with differently sized and/or shaped voids in a uniform or non-uniform pattern or generally uniform voids arranged in a non-uniform pattern.

As in the embodiments described above, inner seal 24 of the embodiment of FIG. 15 may include layers or bands made up of the outer housing materials, materials of the filter medium 30 including the materials of the first, second and third filter elements and/or composites thereof. Thus, as shown in FIG. 15, inner seal 24 may include, in the direction of flow, a first layer 37' made up at least substantially entirely of the inlet housing material, such as polyvinyl chloride. Downstream of layer 37' is a second layer 44' that may be a composite of the housing material and the first and possibly also the second elements or regions 32' and 34' (see FIG. 14). Downstream of layer 44' is preferably a layer or band 46' which at least substantially includes the material of filter element 34', i.e., the material(s) of the filter medium for removing leukocytes.

Next, the seal region may include a band or layer 48' which may be a composite of the material of the third filter element 36', 36" (and/or frame 42 thereof) the material of the outer housing wall 16, if the material of the third element is different from the material of the housing wall. Composite layer 48' may be followed by and adjacent to a layer 39' that includes primary or at least substantially the material of outer housing wall 16.

In an embodiment, such as for example, where the third filter element is a mesh (with or without a frame region) as described in connection with FIGS. 13-17, the material of the third element may be identical to the material of the outer housing wall (e.g., polyvinyl chloride). In this embodiment, the seal may be devoid of composite layer made up of the third filter element and outer housing wall 16. In this embodiment, the downstream most layer or band may be present as an undifferentiated layer, band or region or aggregate of the common material. In one embodiment, a (molten) layer 46' of the second filter element 34' may be at least substantially excluded from central region 38' of inner seal 24 (and 26) such that a more downstream layer (e.g., the third element/outlet housing commingled layer), band or region may be adjacent to the upstream composite layer 44' described above in at least central section 38'. In one embodiment, this may be achieved by a sealing process in which the commingled and typically undifferentiated layer or region at least substantially displaces the layer of molten main filter material 46' toward and into peripheral sections 41. A more detailed discussion of a seal utilizing a mesh element of the type described above, the characteristics of the bands or layers within the inner seal, and methods for forming such a seal are set forth in a simultaneously filed U.S. Patent Application Publication No. 2015/0265758, the contents of which are incorporated by reference herein.

Figures 18, 19:
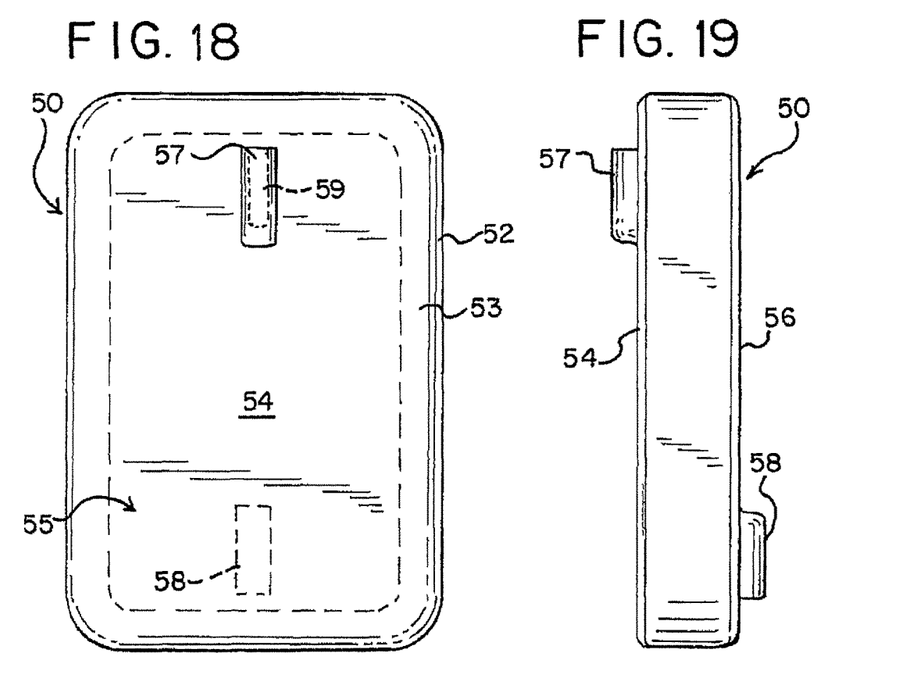
FIG. 18 is plan view of another embodiment of a filter assembly in accordance with the present disclosure.
FIG. 19 side view of the filter assembly of FIG. 18.
Figure 20:
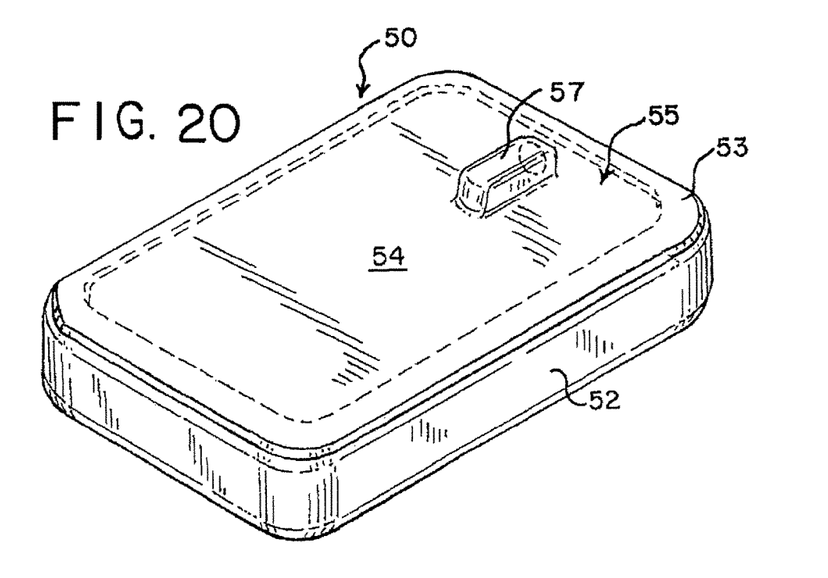
FIG. 20 is a perspective view of the filter assembly of FIGS. 18-19.
Figure 21:
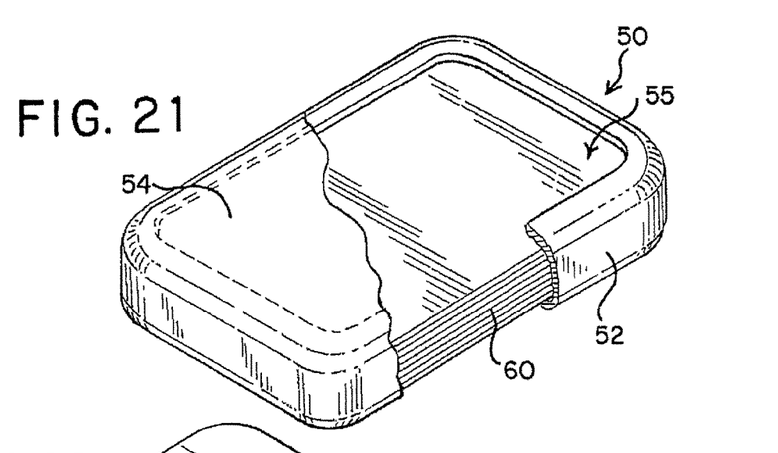
FIG. 21 is a further perspective view of the filter assembly of FIGS. 18-19 with a portion of a flexible housing wall and a portion of the molded frame broken away.

FIG. 18 shows an alternative embodiment of a filter assembly 50 in accordance with the present disclosure. As shown in FIGS. 18-21, filter assembly 50 includes a frame 52 that houses filter medium 60, described in greater detail below. Frame 52 includes a rim 53 that defines a central opening 55 with walls 54 and 56 located at the inlet side and the outlet side of filter assembly (as defined by the placement of the inlet and outlet ports described below). Frame 42 and, for that matter, rim 53 and central opening 55 may be rectangularly-shaped, but may also have other shapes such as a square, circle, oval, triangle, diamond, etc. Walls 54 and 56 may be made of any flexible medical grade polymeric material that is impermeable to liquid including, but not limited to, plasticized polyvinyl chloride (PVC).

As in the previous embodiments described above, walls 54 and 56 may carry inlet and outlet ports 57 and 58, respectively. Ports 57 and 58 define flow paths 59 that allow liquid introduction into and liquid withdrawal from filter assembly 50.

Filtration medium 60 (FIGS. 21-22) may be provided as a stack or pad of selectively porous sheets substantially as described above in connection with the earlier embodiments of FIG. 1-17. Thus, filter medium 60 may include at least first and second regions such as a first (pre-filter) element and a second (main filter) element. A third filter element 36 may optionally be included, but more preferably is not included. In an alternative embodiment, frame 52 may be molded with ribs to space filter medium 60 from outlet housing wall 56. Materials suitable for the different elements include, but are not limited to PBT, PET and PP and the thicknesses of the sheets or plurality of sheets may be as previously described.

Unlike the embodiments of FIGS. 1-17, the filter assembly of FIG. 18 does not require and typically does not include internal seals (24 and/or 26), although some joining of the filter elements by welding or adhesion may be employed. Accordingly, filter assembly 50 does not have layers or bands within a seal that includes composites of two or more materials, or a cushioned periphery. With a molded frame, filter assembly would likewise not include an outer peripheral seal of flexible housing walls 54 and 56.

Figures 22, 23:
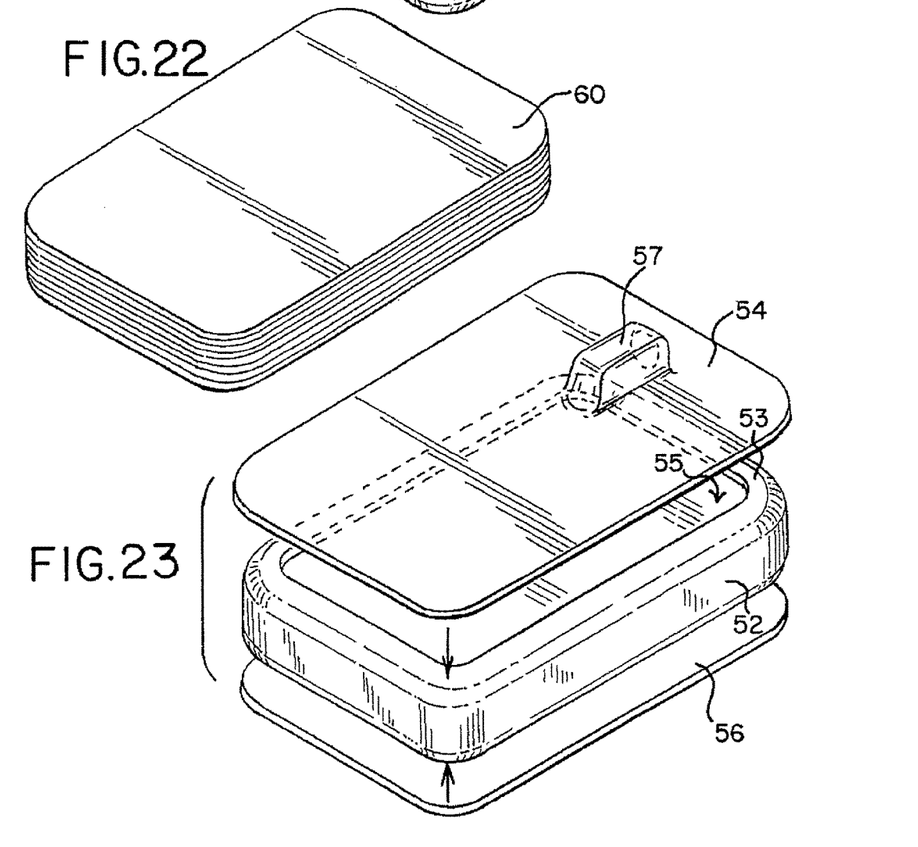
FIG. 22 is a perspective view of the filter stack (of filter media sheets) in the filter assembly of FIGS. 18-19.
FIG. 23 is a perspective view of the filter assembly of FIGS. 18-20 prior to attachment of the flexible outlet and inlet housing walls.
Figures 24, 25:
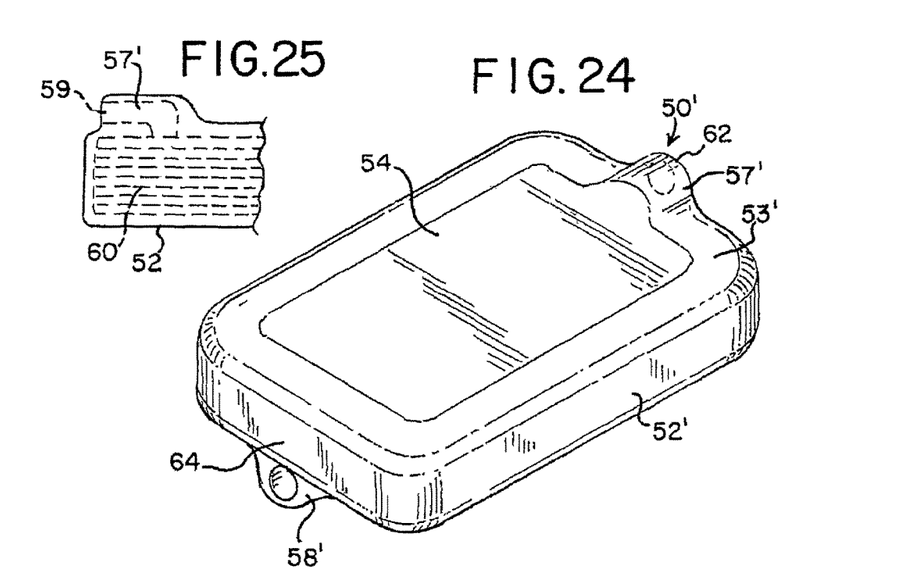
FIG. 24 is a perspective view of still another embodiment of a filter assembly in accordance with the present disclosure.
FIG. 25 is a partial view of the filter assembly of FIG. 24 with a port in the molded frame.
Figures 26, 27, 28:
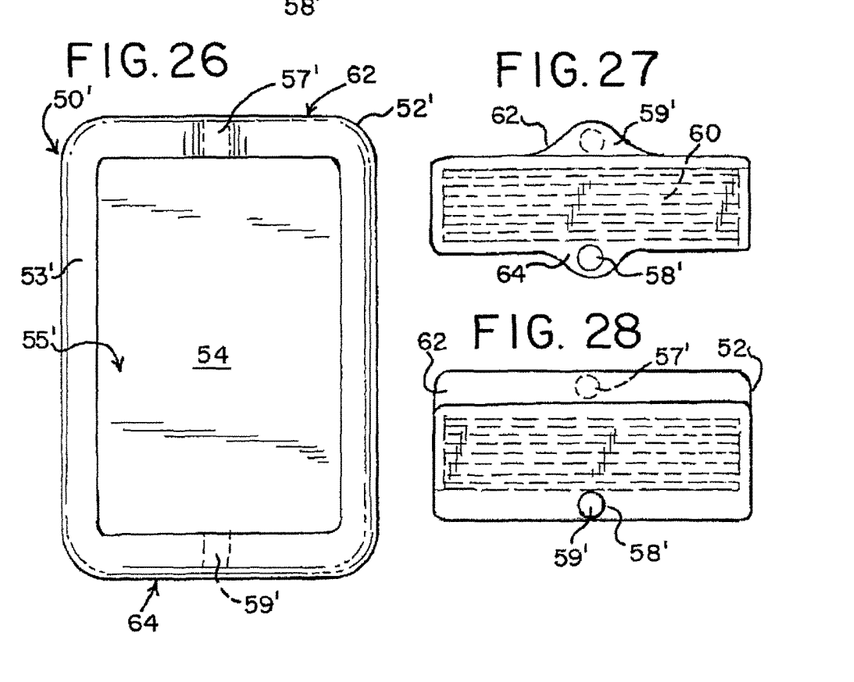
FIG. 26 is a top, plan view of the filter assembly of FIGS. 24-25.
FIG. 27 is an end view of the embodiment of the filter assembly of FIGS. 24-26.
FIG. 28 is an end view of an alternative embodiment of the filter assemblies of FIGS. 18-26.

In accordance with the present disclosure, frame 52 may be molded such as by injection molding. More particularly, frame 52 may be insert molded such that the outer edges of the filter medium 60 pad or stack (and in the embodiment described in the preceding paragraph, the flexible housing walls) are contained and captured within the frame, as shown for example in FIG. 21. Frame 52 may be molded from any suitable polymeric material. In one embodiment, frame 52 may be molded from polyvinyl chloride (PVC). Other suitable materials include polyester, hytrel and other material suitable for RF or thermal induced welding. Flexible walls 54 and 56 may be attached to frame 52 by, for example, welding or adhesion preferably along the entirety of rim 53 of both the front and rear of frame 52, i.e., at the inlet side and the outlet side of frame 52. As shown in FIG. 23, ports may be pre-attached to flexible walls 54 and 56.

In another alternative, rather than sealing flexible housing walls 54 and 56 to frame 52 over central opening 55, flexible housing walls 54 and 56 may be "stacked" and joined with the sheets of the filter medium 60 around which frame 52 is molded. Thus, flexible housing 52 and 54 with or without ports 57 and 58 are captured with filter medium 60 by the molded frame 52.

Also, in an alternative embodiment of filter assembly 50', shown in FIGS. 24-28, ports 57' and 58' may be integral with frame 52' and not pre-attached to walls 54 and 56. More particularly, ports 57' and 58' may be integrally formed (i.e., molded) with frame 52'. Thus ports 57' and 58' shown in FIGS. 24-28 define flow paths 59' through frame 52. Ports 57' and 58' define apertures at opposing ends 62 and 64 of frame 52' for connection or attachment with tubing of a blood collection set. Flexible walls 52 and 54 are attached to the outer surface of frame 52' along rim 53' or, alternatively may be pre-assembled with filter medium and captured by frame 52 during the insert molding process, as described above.

Figure 29:
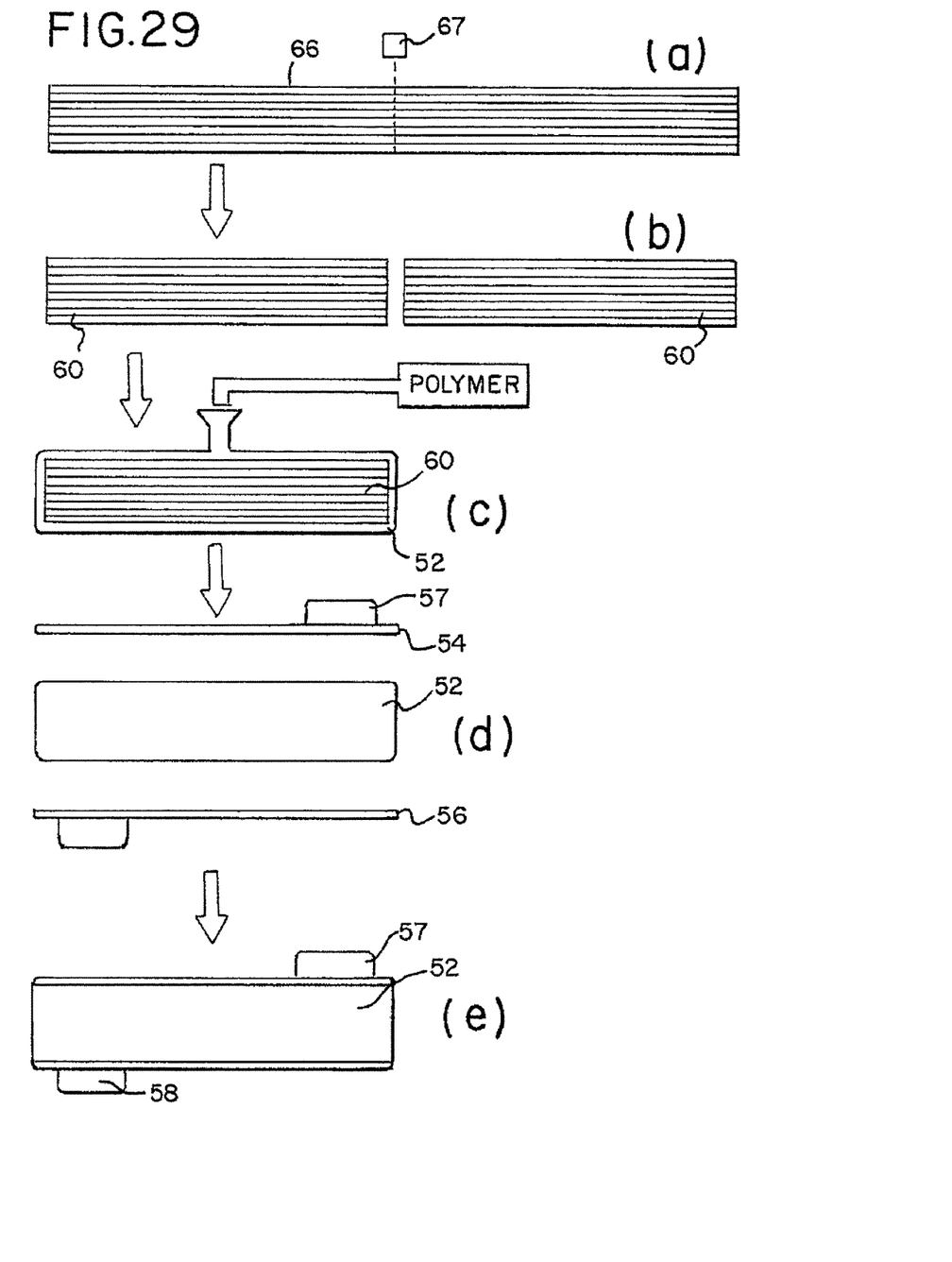

As shown in FIG. 29, filter assembly 50 (or 50') may be assembled as follows. A sheet 66 of multi-layered filter media 60 is provided and segmented into individual, smaller-sized pads 60. Pads 60 may be segmented by cutting, as seen in FIG. 29(b). Individual pads 60 may then be inserted into a mold 61 for molding with an injected molten polymer (See FIG. 29(c)). Once the molded frame has cooled, filter subassembly 50 is removed from the mold. Flexible housing sheets 54 and 56 (with or without pre-attached inlet and outlet ports 57 and 58) may then be attached to frame 52'. Alternatively, flexible housing sheets 54 and 56 may be joined to the filter stack prior to molding of the frame. It will be appreciated that frame 52 may include integrally molded ports as shown in FIGS. 25-28, in which case flexible housing sheets would not include pre-attached ports.

EXAMPLES

Without limiting any of the foregoing, the subject matter described herein may be found in one or more apparatus. For example, in a first aspect of the present subject matter includes a biological fluid filter assembly including (a) a molded frame comprising a rim defining a central opening, said frame comprising an inner surface and an outer surface and an inlet side and an outlet side; (b) a filter medium comprising a plurality of stacked sheets captured by said frame; (c) at least one inlet and one outlet port; and (d) first and second flexible housing walls at said inlet side and at said outlet side.

A second aspect of the present subject matter includes a filter assembly in accordance with the first aspect described above wherein the first and second flexible housing walls are joined to said frame at the outer surfaces of the inlet and outlet sides.

A third aspect of the present subject matter includes a filter assembly in accordance with any of the first through second aspects described above wherein the stack is spaced from said inner surface of said frame at said outlet side.

A fourth aspect of the present subject matter includes a filter assembly in accordance with the third aspect described above the inner surface of said frame at said outlet side comprises one or more spacer elements.

A fifth aspect of the present subject matter includes a filter assembly in accordance with any one of the first through fourth aspects described above wherein there is no direct seal between a flexible housing wall and the filter stack.

A sixth aspect of the present subject matter includes a filter assembly in accordance with any one of the first through fifth aspects described above there is no direct seal between the first and second flexible housing walls.

A seventh aspect of the present subject matter includes the biological fluid filter assembly of any one of the first through sixth aspects wherein the inlet port is attached to the sheet that is attached to the frame on the inlet side and the outlet port is attached to the flexible sheet that is attached to the outlet side.

An eighth aspect of the present subject matter includes the biological fluid filter assembly of any one of the first through sixth aspects wherein the inlet port and outlet port are integrally molded with the frame.

A ninth aspect of the present subject matter includes the biological fluid filter assembly of any one of the first through eighth aspects wherein the frame is made of polyvinyl chloride.

A tenth aspect of the present subject matter includes the biological fluid filter assembly of any one of the first through ninth aspects wherein at least one of the flexible sheets is made of material that includes polyvinyl chloride.

An eleventh aspect of the present subject matter includes the biological fluid filter assembly of any one of the first through tenth aspects wherein the filter medium includes first and second filter regions.

A twelfth aspect of the present subject matter includes the biological fluid filter assembly of the eleventh aspect wherein at least one of the filter regions is made of a non-woven, fibrous material having a porosity suitable for removing leukocytes from blood or a blood component.

A thirteenth aspect of the present subject matter includes the biological fluid filter assembly of any one of the eleventh and twelfth aspects wherein one of the filter regions is made of a non-woven, fibrous material having a porosity suitable for removing microaggregates from blood or a blood component.

A fourteenth aspect of the present subject matter includes the biological fluid filter assembly of any one of the eleventh through thirteenth aspects wherein at least one of the regions includes a melt blown material selected from the group of polyethylene terephthalate, polybutylene terephthalate and polypropylene.

A fifteenth aspect of the present subject matter includes a method for making a filter with flexible housing walls including the steps of (a) locating a filter medium defining and outer peripheral edge and comprising an inlet side and an outlet side in the cavity of a molding apparatus (b) introducing a molten polymeric material into said cavity to form a frame around said peripheral edge of said filter medium, said frame defining a pair of central openings at said inlet and outlet sides of said medium (c) locating a flexible housing wall at said inlet side of the frame and locating a flexible housing wall at an outlet side of the frame.

A sixteenth aspect of the present subject matter includes the method in accordance with the fifteenth aspect and further including attaching ports to each of the flexible housing walls.

A seventeenth aspect of the present subject matter includes the method in accordance with any one of the fifteenth through sixteenth aspects and further comprising forming said filter medium by assembling a stack of porous sheets.

An eighteenth aspect of the present subject matter includes the method in accordance with the seventeenth aspect further comprising cutting the stack to provide a filter pad.

A nineteenth aspect of the present subject matter includes the method of any one of the preceding fifteenth through eighteenth aspects wherein the molten polymeric material comprises polyvinyl chloride.

A twentieth aspect of the present subject matter includes the method of any one of the preceding fifteenth through nineteenth aspects wherein the method further includes forming an inlet port and an outlet port in the frame.

It will be understood that the embodiments and examples described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope of the invention(s) is not limited to the above description but is as set forth in the following claims, and it is understood that claims may be directed to the features hereof, including as combinations of features that are individually disclosed or claimed herein.

The invention claimed is:

1. A biological fluid filter assembly comprising:
   a) a molded frame having an inlet side and an outlet side and comprising a rim defining a central opening in said inlet side and a central opening in said outlet side, said frame comprising an inner surface and an outer surface;
   b) a single filter medium comprising a plurality of stacked sheets, said stacked sheets having outer edges which are captured by and enclosed within said frame;
   c) at least one inlet port at said inlet side and one outlet port at said outlet side; and
   d) a first flexible sheet defining a housing wall adjacent to said frame at said central opening at said inlet side and a second flexible sheet defining a housing wall adjacent to said frame at said central opening at said outlet side of said frame.

2. The biological fluid filter of claim 1 wherein said first and second flexible sheets defining said housing walls are joined to said frame at the outer surfaces of said inlet and outlet sides, respectively.

3. The biological fluid filter of claim 1 wherein said stacked sheets spaced from said inner surface of said frame at said outlet side.

4. The biological fluid filter of claim 1 wherein there is no direct seal between a flexible housing wall and said filter medium.

5. The biological fluid filter of claim 1 wherein there is no direct seal between said first and second flexible housing walls.

6. The biological fluid filter assembly of claim 1 wherein said inlet port is attached to said first flexible sheet that is adjacent to said frame at said inlet side and said outlet port is attached to said second flexible sheet that is adjacent to said frame at said outlet side.

7. The biological fluid filter assembly of claim 1 wherein said inlet port and said outlet port are in said frame.

8. The biological fluid filter assembly of claim 1 wherein said frame comprises polyvinyl chloride.

9. The biological fluid filter assembly of claim 1 wherein at least one of said flexible sheets is made of a material comprising polyvinyl chloride.

10. The biological fluid filter assembly of claim 1 wherein said filter medium comprises first and second filter regions.

11. The biological fluid filter assembly of claim 10 wherein at least one of said filter regions comprises a non-woven fibrous material having a porosity suitable for removing leukocytes from blood or a blood component.

12. The biological fluid filter assembly of claim 10 wherein one of said filter regions comprises a non-woven, fibrous material having a porosity suitable for removing microaggregates from blood or a blood component.

13. The biological fluid filter assembly of claim 10 wherein at least one of said filter regions includes a melt blown material selected from the group of polyethylene terephthalate, polybutylene terephthalate and polypropylene.

14. The filter assembly of claim 1 wherein flow through said assembly proceeds from said inlet port, through said single filter medium to said outlet port.

15. The filter assembly of claim 1 wherein said frame and said first and second flexible walls define a single chamber housing said single filter medium.

16. The filter assembly of claim 1 wherein said stacked sheets are arranged one on top of next from the one of the inlet side and outlet side to the other of said inlet side and said outlet side.

17. The filter assembly of claim 1 wherein said first and second housing walls are attached to the outer surface of said frame rim.

18. The filter assembly of claim 1 wherein said first and second housing walls are captured within the said frame.

19. The filter assembly of claim 18 wherein said first and second flexible housing walls separate said filter medium from said frame.

20. The filter assembly of claim 17 wherein said frame rim is located between said flexible housing walls and said filter medium.

21. The filter assembly of claim 1 wherein said frame comprises a unitary, one-piece frame.

\* \* \* \* \*